United States Patent [19]

Reinhard

[11] Patent Number: 4,728,197

[45] Date of Patent: Mar. 1, 1988

[54] APPARATUS FOR PRODUCTION OF MOLDING MATERIALS

[76] Inventor: Peter Reinhard, Weingartenstrasse 8, Spreitenbach, Switzerland

[21] Appl. No.: 876,174

[22] Filed: Jun. 19, 1986

[30] Foreign Application Priority Data

Jun. 20, 1985 [CH] Switzerland .................. 2628/85

[51] Int. Cl.⁴ .............................................. B01F 9/00
[52] U.S. Cl. .................................................... 366/219
[58] Field of Search ............... 366/208, 219, 287, 602

[56] References Cited

U.S. PATENT DOCUMENTS

| | | | |
|---|---|---|---|
| 1,661,681 | 3/1928 | Rood | 366/602 |
| 3,591,098 | 7/1971 | McShirley | 366/602 |
| 3,985,307 | 10/1976 | Ebbert et al. | 366/602 |
| 4,125,335 | 11/1978 | Blume et al. | 366/602 |

FOREIGN PATENT DOCUMENTS 2713152  3/1977  Fed. Rep. of Germany .
3022689  6/1980  Fed. Rep. of Germany .

*Primary Examiner*—Harvey C. Hornsby
*Assistant Examiner*—Corinne M. Reinckens
*Attorney, Agent, or Firm*—Helfgott & Karas

[57] ABSTRACT

The present invention relates to an apparatus for producing molding or impression materials, particularly for dental use, by mixing dry powder and liquid in a container mounted on a rotary arm being driven by two pair of gears, connecting the motor shaft of the driving motor to the rotatable container.

6 Claims, 2 Drawing Figures

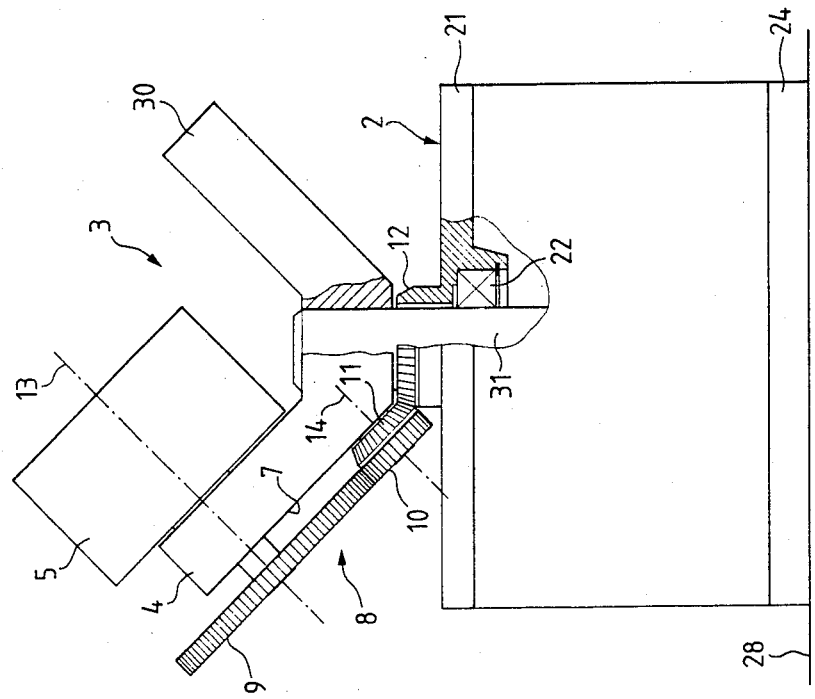
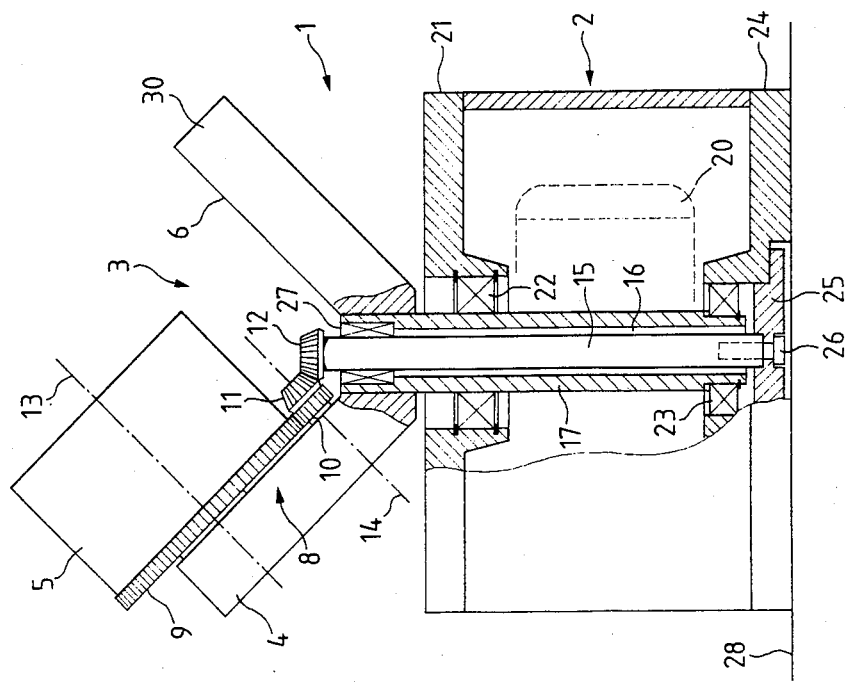

APPARATUS FOR PRODUCTION OF MOLDING MATERIALS

BACKGROUND OF THE INVENTION

Various apparatus are known which are suitable for mixing molding or impression materials such as are used in the dental field. The equipment used to mix the dry materials and liquid should permit such mixing to occur without bubble formation.

German DE-OS No. 27 13 152 discloses a mixing apparatus for dental molding materials having a mixing cup with openings into which the fingers of the mixing apparatus project. Additional fingers are arranged in the mixing cup cover and these are spaced with respect to the former fingers. The molding material is mixed by rotating the fingers of the mixing apparatus. However, poor and incomplete mixing is obtained because of the movement of the rotating fingers in the mixing zone resulting in a non-uniform molding material. German DE-OS No. 30 22 689 disclosed another mixer wherein the mixing cup is constructed as a dish with an annular channel having a V-shaped profile and into which a rotating counter-cone projects with a vertical rotating axis. Mixing takes place by rotating the dish and counter-cone. Driving takes place with the aid of envelope drives, both for the counter-cone and the dish. The apparatus has relatively complicated construction and due to the special shape of the dish, is large.

OBJECTS OF THE INVENTION

The object of the invention is to provide an apparatus for producing molding materials having a simple construction. It is a further object of the invention to provide an apparatus for producing molding materials which has a trouble free, durable mixing cup.

DESCRIPTION OF THE INVENTION

The objects of the present invention may be attained by use of an apparatus where the rotary arm supporting the mixing vessel rotates counter to the mixing vessel and the arm is fixed to the motor shaft, the mixing vessel mounted on the arm is driven by rotary toothed gear means wherein one pair of gears is mounted on the rotary arm, one gear of the pair being arranged centrally with the axis of the mixing vessel and the other gear of the pair eccentrically with respect to the axis to ensure driving of the mixing vessel with substantially no free-play.

BRIEF DESCRIPTION OF THE DRAWINGS

The invention is described in greater detail hereinafter with respect to two preferred embodiments and the attached drawings wherein:

FIG. 1 is a vertical sectional view, cut-away to show the apparatus employing an epicyclic gear arranged on the inside of the rotary arm to drive the mixing vessel:

FIG. 2 is a vertical sectional view, cut-away to show the apparatus employing an epicyclic gear arranged on the outside of the rotary arm to drive the mixing vessel.

The two embodiments of the present invention shown in FIGS. 1 and 2 have an identical mixing action since in both cases the arrangement and rotation of the vessel are the same.

Referring now to the drawings, FIG. 1 shows apparatus 1 having a casing 2 which also serves as a base for the apparatus. Mixer 3 is mounted above casing 2 and compises rotary arm 4, mixing vessel 5 mounted on rotary arm 4 and epicyclic gear 8 arranged on the inside of rotary arm 4 provides for counter rotation of mixing vessel 5 and rotary arm 4. Epicyclic gear 8 comprises a first pair of gears 9,10 and a second pair of gears 11,12. Gear 9 is positioned centrally with respect to rotational axis 13 of mixing vessel 5. Mixing vessel 5 is mounted on and is rotationally inter-connected with gear 9 (mounting support not shown). Gear 10 has a rotational axis 14, which is eccentric but parallel to rotational axis 13. Gear 10 carries gear 11 of the second gear pair which is a bevel gear. Gear 12 is also a bevel gear, so that the two gears 11, 12 form a miter gear. Gear 12 is fixed to the end of stationary shaft 15 which extends through rotary arm 4. Stationary shaft 15 is axially located within bore 16 of hollow shaft 17 which forms the drive shaft of rotary arm 4. Hollow shaft 17 is part of electric motor 20 housed in casing 2 which rotates both rotary arm 4 and mixing vessel 5 by means of epicyclic gear 8.

Casing 2 has a cover 21 having a bearing 22, e.g., an anti-friction bearing for supporting hollow shaft 17. A further bearing 23 is provided in base 24 of casing 2 to support hollow shaft 17. Base 24 has a cover 25 which holds stationary shaft 15 by means of screw 26. Stationary shaft 15 has gear 12 mounted thereon and is supported relative to hollow shaft 17 by bearing 27. Casing 2 can be appropriately supported on a work surface 28 so that rotation of casing 2 during operation of mixing apparatus 1 is prevented.

When operating the mixer, mixing vessel 5, charged with the dry powder and liquid, is mounted on rotary arm 4 and motor 20 is started. Gear 11 rolls on fixed gear 12 so that through gear 10, gear 9 and therefore mixing vessel 5 are rotated. As a result of the construction of the epicyclic gear, mixing vessel 5 rotates counter to the rotational direction of rotary arm 4. Rotary arm 4 is also provided with an opposing second rotary arm 30 which serves as a counter weight for rotary arm 4 with mixing vessel 5 mounted thereon.

In the embodiment of the invention shown in FIG. 2, a simplification is shown wherein a hollow shaft is not required. Drive shaft 31 of the electric motor (not shown) arranged in casing 2 projects above cover 21 and carries rotary arm 4 and opposing rotary arm 30. The essential difference betweeen the two embodiments is in the location of epicyclic gear 8, which is mounted on the outside surface 7 of rotary arm 4. Stationary gear 12 circumscribes drive shaft 31 in an annular manner and is fixed to cover 21. Gear 10 and gear 11 are mounted as in FIG. 1 on an axis 14 eccentric to the rotational axis 13 of mixing vessel 5, while gear 9 is positioned centrally with respect to rotational axis 13 of mixing vessel 5. A bearing 22, e.g. an anti-friction bearing, is provided in cover 21 and supports drive shaft 31 in the cover.

The two embodiments are primarily intended for use in producing dental molding materials, e.g., for mixing alginate powder and water, as well as single or multi-component pastes. This permits rapid and uniform mixing of molding materials for producing jaw and tooth impressions in a bubble free manner. The epicyclic gear can be strengthened to provide a reliable, durable apparatus.

Although the invention has been described with respect to mixing dental molding materials, it will be obvious to those skilled in the art that the appparatus will also be useful for mixing other materials.

What is claimed is:

1. Apparatus for mixing a powder and a liquid, said apparatus comprising: a hollow casing;

an electric motor mounted in the casing, said motor having a vertical first drive shaft having a vertical hollow channel extending completely therethrough, the first shaft and channel having a common vertical axis which is a first axis of rotation, the first shaft being rotated about the first axis when the motor is operative, said first shaft having an upper end extending out of and above the casing;

first and second oppositely disposed arms extending inclinedly upwards in counter-balancing position from a common portion having inner surfaces likewise inclined and facing each other, the bottom portion having a vertical bore in which the upper end of the first shaft is disposed, the bore having an axis aligned with the first axis, the first shaft being secured to the bottom portion, the arms with said portion being spaced above the casing so that rotation of the first shaft causes said arms to rotate about the first axis, each arm serving as a counterbalance for the other;

a second vertical shaft disposed non-rotatably in said channel, the second shaft being axially aligned with and spaced from the first shaft, the second shaft extending through the vertical bore and having an upper end disposed above the common portion, the second shaft being spaced from said arms;

a hollow cylindrical mixing vessel having a second axis of rotation whch extends at right angles to the inner surface of one of said arms and is not parallel to the first axis, said powder and said liquid being mixed in this vessel;

first means securing the vessel to the inner surface of said one arm, the first means and the vessel being rotatable together about the second axis; and second means coupled to the first means and to the upper end of the second shaft to cause the vessel to rotate about the second axis when the first shaft is rotated about the first axis.

2. Apparatus as set forth in claim 1 wherein said first means is a first gear disposed between the vessel and the one arm and rotatable about the second axis.

3. Apparatus as set forth in claim 2 wherein the second means includes a second gear secured non-rotatably to the upper end of the second shaft.

4. Apparatus as set forth in claim 3 wherein the second means includes a third gear engaging the second gear and a fourth gear engaging the first gear, the third and fourth gears being rotatable about a third axis of rotation spaced from and parallel to the second axis of rotation.

5. Apparatus as set forth in claim 4 wherein the third and fourth gears are connected together.

6. Apparatus as set forth in claim 4 wherein the second and third gears are meshing bevel gears.

* * * * *